United States Patent [19]

Boigegrain et al.

[11] 4,193,997
[45] Mar. 18, 1980

[54] THIENO[2,3-c] AND [3,2-c]PYRIDINES, PROCESS FOR THEIR PREPARATION AND THERAPEUTIC APPLICATIONS THEREOF

[75] Inventors: Robert Boigegrain, Portet; Michel Gachon, Ramonville St Ague; Jean-Pierre Maffrand; Gérard Maire, both of Toulouse, all of France

[73] Assignee: Parcor, Paris, France

[21] Appl. No.: 886,688

[22] Filed: Mar. 15, 1978

[30] Foreign Application Priority Data

Mar. 29, 1977 [GB] United Kingdom ............... 13209/77

[51] Int. Cl.² ................. C07D 471/04; A61K 31/435
[52] U.S. Cl. ..................................... 424/256; 546/114
[58] Field of Search ................. 260/294.8 C; 424/256; 546/114

[56] References Cited

PUBLICATIONS

Aparajithan et al., Journal of Heterocyclic Chemistry, vol, 3, pp. 446–469 (1966).

*Primary Examiner*—Alan L. Rotman
*Attorney, Agent, or Firm*—Young & Thompson

[57] ABSTRACT

This invention relates to compounds having the formulae

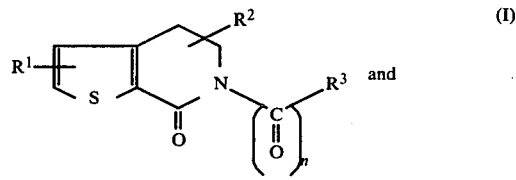

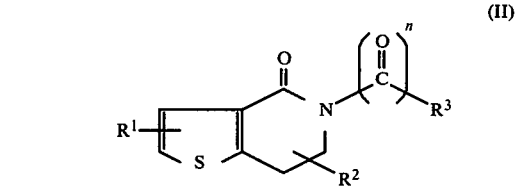

in which:
  $R^1$ represents hydrogen, a halogen atom or a lower alkyl radical, a lower alkoxy radical or a lower alkylthio radical;
  $R^2$ represents hydrogen or a lower alkyl, aralkyl, aryl, carboxy or alkoxycarbonyl radical;
  $R^3$ represents hydrogen, a $C_{1-12}$ alkyl radical, or an aralkyl or aryl radical, optionally substituted on the aromatic nucleus with one or more halogen atoms or hydroxy, nitro, cyano, carboxamido, carboxy, alkoxycarbonyl, lower alkyl, lower alkoxy or trifluoromethyl groups; and
  n is zero or 1.

Said new compounds possess therapeutically useful blood-platelet aggregation inhibiting properties and also anti-thrombotic, anti-sludge, antalgic and anti-inflammatory properties.

10 Claims, No Drawings

THIENO[2,3-C] AND [3,2-C]PYRIDINES, PROCESS FOR THEIR PREPARATION AND THERAPEUTIC APPLICATIONS THEREOF

This invention relates to new thienopyridine derivatives, to a process for their preparation and to their applications in human and veterinary medicine.

The new compounds of this invention have one of the following general formulae:

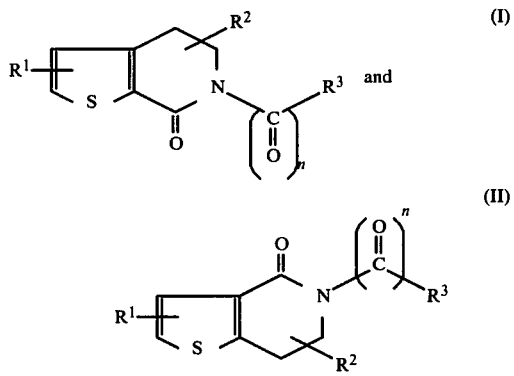

in which:
- $R^1$ represents hydrogen, a halogen atom or a lower alkyl radical, a lower alkoxy radical or a lower alkylthio radical;
- $R^2$ represents hydrogen or a lower alkyl radical, an aralkyl radical, an aryl radical, a carboxy radical or an alkoxycarbonyl radical;
- $R^3$ represents hydrogen, a $C_{1-12}$ alkyl radical, or an aralkyl or aryl radical, optionally substituted on the aromatic nucleus with one or more halogen atoms or hydroxy, nitro, cyano, carboxamido, carboxy, alkoxycarbonyl, lower alkyl, lower alkoxy or trifluoromethyl groups; and
- n is zero or 1.

By "lower alkyl" or "lower alkoxy" are meant here groups having 1–6 carbon atoms, preferably 1–4 carbon atoms.

This invention relates also to a process for the preparation of the compounds of the formula (I) or (II) as defined above, comprising oxidizing compounds of the formula (III) or (IV), respectively:

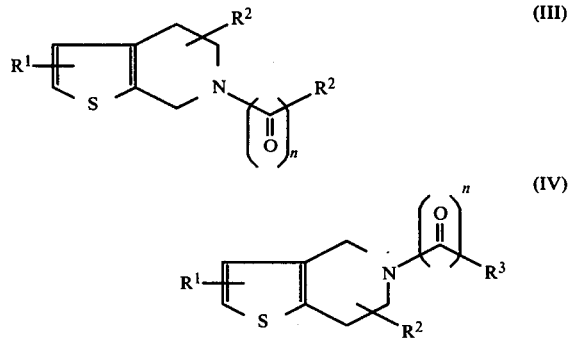

in which $R^1$, $R^2$, $R^3$ and n have the above-defined meanings.

The oxidation reaction is typically effected with an alkali metal permanganate such as potassium permanganate.

The reaction may be effected by heating the reagents in acetone, at a temperature within the range from 40° to 56° C., or at room temperature, in a two-phase water-benzene system while using a quaternary ammonium salt as phase transfer catalyst.

According to a modification, the compounds of the formula (I) and (II) in which n=0 and $R^3$=H may also be obtained by acid hydrolysis of the corresponding imides of the formulae (I) and (II) (n=1; $R^3$=anyone of the aforesaid meanings except H).

The starting materials of the formulae (III) and (IV) may be prepared as described in the following patents and publications: U.S. Pat. Nos. 4,051,141; 4,075,340; 4,097,482; 4,104,390; and J. P. Maffrand & F. Eloy, Eur. J. Med. Chem.-Chimica Therapeutica, 1974, 9 (5), 483.

The following non limiting Examples illustrate this invention.

All temperatures are in degrees Celsius.

EXAMPLE 1

4-Oxo-5-o.chlorobenzyl-4,5,6,7-tetrahydro-thieno[3,2-c]pyridine (Derivative n°1)

To a stirred solution of 5-o.chlorobenzyl-4,5,6,7-tetrahydro-thieno[3,2-c]pyridine (6.5 g; 24.6 mmoles) in acetone (250 ml) heated at 40° C., is added portionwise finely powdered potassium permanganate (15.59 g; 98.6 mmoles). The reaction causes the refluxing of the solvent. On completion of the addition, the reaction mixture is maintained at 40° C. for a further 30 minutes, after which it is cooled and filtered through a silica bed. The filtrate is evaporated to dryness, and the resulting solid material is recrystallized from diisopropyl ether, to give white crystals, M.p.=60° C. (Yield: 55%).

EXAMPLE 2

4-Oxo-5-benzyl-4,5,6,7-tetrahydro-thieno[3,2-c]pyridine (Derivative n°2)

The compound is prepared according to the procedure of Example 1, from 5-benzyl-4,5,6,7-tetrahydro-thieno[3,2-c]-pyridine, to give white crystals, M.p.=54° C.; $B.p._{0.05}$=115° C. (Yield: 64%).

EXAMPLE 3

4-Oxo-5-p.chlorobenzyl-4,5,6,7-tetrahydro-thieno[3,2-c]pyridine (Derivative n°3)

The compound is prepared according to the procedure of Example 1, from 5-p.chlorobenzyl-4,5,6,7-tetrahydro-thieno[3,2-c]-pyridine, to give white crystals, M.p.=120° C. (ethanol-diisopropyl ether). Yield: 66%.

EXAMPLE 4

6-o.Chlorobenzyl-7-oxo-4,5,6,7-tetrahydro-thieno[2,3-c]-pyridine (Derivative n°4)

The compound is prepared according to the procedure of Example 1, from 6-o.chlorobenzyl-4,5,6,7-tetrahydro-thieno[2,3-c]pyridine, to give pale yellow crystals, M.p. 80° C. (diisopropyl ether), Yield: 45%.

EXAMPLE 5

4-Oxo-5-acetyl-4,5,6,7-tetrahydro-thieno[3,2-c]pyridine (Derivative n°5)

The compound is prepared according to the procedure of Example 1, from 5-acetyl-4,5,6,7-tetrahydro-thieno[3,2-c]-pyridine, to give ivory coloured crystals, M.p. 90° C. (diisopropyl ether), Yield: 46%.

EXAMPLE 6

4-Oxo-5-o.chlorobenzoyl-4,5,6,7-tetrahydro-thieno[3,2-c]pyridine (Derivative n°6)

The compound is prepared according to the procedure of Example 1, from 5-o.chlorobenzoyl-4,5,6,7-tetrahydro-thieno[3,2-c]pyridine, to give white crystals, M.p.=148° C. (ethanoldiisopropyl ether), Yield: 57%.

EXAMPLE 7

4-Oxo-4,5,6,7-tetrahydro-thieno[3,2-c]pyridine (Derivative n°7)

An initially heterogeneous mixture of 4-oxo-5-acetyl-4,5,6,7-tetrahydro-thieno[3,2-c]pyridine (13.6 g; 0.069 mole) from Example 5, ethanol (50 ml) and 6 N hydrochloric acid (50 ml) is stirred for 4 hours at room temperature. The reaction mixture is concentrated in vacuo, the residue is made slightly basic by addition of sodium hydroxide and is then extracted with methylene chloride. The organic extracts are washed with water, dried over sodium sulfate and evaporated to dryness. The resulting residue is recrystallized from isopropanol-diisopropyl ether, to give white crystals, M.p.=94° C. Yield: 70%.

EXAMPLE 8

4-Oxo-5-o.cyanobenzyl-4,5,6,7-tetrahydro-thieno[3,2-c]pyridine (Derivative n°8)

The compound is prepared according to the procedure of Example 1, from 5-o.cyanobenzyl-4,5,6,7-tetrahydro-thieno[3,2-c]pyridine, to give white crystals, M.p.=115° C. (diisopropyl ether-isopropanol), Yield: 69%.

EXAMPLE 9

4-Oxo-5-o,carbomethoxybenzyl-4,5,6,7-tetrahydro-thieno[3,2-c]-pyridine (Derivative n°9)

The compound is prepared according to the procedure of Example 1, from 5-o.carbomethoxy-4,5,6,7-tetrahydro-thieno[3,2-c]pyridine, to give white crystals, M.p. 98° C. (diisopropyl ether-isopropanol), Yield: 61%.

EXAMPLE 10

6-o.Chlorobenzoyl-7-oxo-4,5,6,7-tetrahydro-thieno[2,3-c]pyridine (Derivative n°10)

The compound is prepared according to the procedure of Example 1, from 6-o.chlorobenzoyl-4,5,6,7-tetrahydro-thieno[2,3-c]pyridine, to give white crystals: M.p. 150° C. (ethanoldiisopropyl ether), Yield: 39%.

EXAMPLE 11

6-Acetyl-7-oxo-4,5,6,7-tetrahydro-thieno[2,3-c]-pyridine (Derivative n°11)

The compound is prepared according to the procedure of Example 1, from 6-acetyl-4,5,6,7-tetrahydro-thieno[2,3-c]pyridine, to give white crystals, M.p.=92° C.; Yield: 43%.

EXAMPLE 12

7-Oxo-4,5,6,7-tetrahydro-thieno[2,3-c]pyridine (Derivative n°12)

The compound is prepared according to the procedure of Example 7, from 6-acetyl-7-oxo-4,5,6,7-tetrahydro-thieno[2,3-c]pyridine (Example 11), to give white crystals, M.p.=120° C. (diisopropyl ether-isopropanol), Yield: 66%.

EXAMPLE 13

4-Oxo-6-benzyloxycarbonyl-5-benzyl-4,5,6,7-tetrahydro-thieno[3,2-c]pyridine (Derivative n°13)

The compound is prepared according to the procedure of Example 1, from 6-benzyloxycarbonyl-5-benzyl-4,5,6,7-tetrahydro-thieno[3,2-c]pyridine, to give white crystals, M.p. 72° C. (cyclohexane), Yield: 53%.

EXAMPLE 14

4-Oxo-6-carboxy-5-benzyl-4,5,6,7-tetrahydro-thieno[3,2-c]-pyridine (Derivative n°14)

The compound is prepared by saponification of 4-oxo-5-benzyloxycarbonyl-5-benzyl-4,5,6,7-tetrahydro-thieno[3,2-c]pyridine (Example 13), to give pink crystals, M.p.=258° C. (isopropanol-ethanol), Yield: 70%.

EXAMPLE 15

4-Oxo-6-(3,4,5-trimethoxy-benzyloxycarbonyl)-5-(3,4,5-trimethoxybenzyl)-4,5,6,7-tetrahydro-thieno[3,2-c]pyridine (Derivative n°15)

The compound is prepared according to the procedure of Example 1, from 6-(3,4,5-trimethoxy-benzyloxycarbonyl)-5-(3,4,5-trimethoxy-benzyl)4,5,6,7-tetrahydro-thieno[3,2-c]-pyridine, to give whitish crystals, M.p. 55° C.; Yield: 48%.

EXAMPLE 16

4-Oxo-6-carboxy-5-(3,4,5-trimethoxy-benzyl)-4,5,6,7-tetrahydro-thieno[3,2-c]pyridine (Derivative n°16)

The compound is prepared by saponification of 4-oxo-6-(3,4,5-trimethoxy-benzyloxycarbonyl)-5-(3,4,5-trimethoxybenzyl)-4,5,6,7-tetrahydro-thieno[3,2-c]pyridine (Example 15), to give beige crystals, M.p.=208° C. (isopropanol), Yield: 65%.

EXAMPLE 17

4-Phenyl-6-acetyl-7-oxo-4,5,6,7-tetrahydro-thieno[2,3-c]-pyridine (Derivative n°17)

The compound is prepared according to the procedure of Example 1, from 4-phenyl-6-acetyl-4,5,6,7-tetrahydro-thieno[2,3-c]pyridine, to give white crystals, M.p.=132° C. (cyclohexane-ethyl acetate), Yield: 20%.

EXAMPLE 18

4-Phenyl-7-oxo-4,5,6,7-tetrahydro-thieno[2,3-c]pyridine (Derivative n°18)

The compound is prepared according to the procedure of Example 7, from 4-phenyl-6-acetyl-7-oxo-4,5,6,7-tetrahydro-thieno[2,3-c]pyridine, to give white crystals, M.p.=160° C. (diisopropyl ether-isopropanol), Yield: 68%.

The following pharmacological and toxicological data are given to show the properties of the derivatives of this invention, particularly their low toxicity and their excellent tolerance, together with their inhibiting activity on blood-platelet aggregation, their anti-thrombotic, anti-sludge, antalgic and anti-inflammatory activity.

Thus, this invention relates also to a therapeutic composition comprising, as active ingredient, a compound of the formula (I) or (II) as defined above.

I. TOXICOLOGICAL INVESTIGATION

The compounds of this invention have an excellent tolerance and a low toxicity. Thus, the $LD_{50}/24$ hrs/kg of animal, as determined in mice according to the method of Miller and Tainter, by the oral route, is in excess of 300 mg for all the derivatives.

In addition, the tests conducted on acute, chronic, subchronic and delayed toxicity in various animal species failed to show any local or systemic reaction, any disorder in the regularly effected biological control tests, any anomaly in the microscopic and macroscopic examinations of the animals sacrificed and autopsied on completion of the experimentation.

II. PHARMACOLOGICAL INVESTIGATION

1. Blood-platelet aggregation inhibiting activity

Blood is taken from the jugular vein of Wistar rats. From this citrated blood, and after centrifugation, a plasma containing 600,000±20,000 blood-platelets per mm 3 is reconstituted, which plasma is used in all aggregation determinations.

(a) Determination of A.D.P.-induced blood-platelet aggregation 0.4 ml plasma is placed in a siliconized tube provided with a magnet bar which is also siliconized. The tube is introduced into an aggregometer connected to an apparatus which records the optical density variations. When light transmission reaches a stable value, 0.5 ml of a solution containing 10 µM A.D.P. (adenosine diphosphate) is introduced into the tube.

Blood-platelet aggregation then induces an increase of light transmission, followed by a decrease subsequent to the disaggregation stage.

The maximal optical density variation thus determined characterizes the extent of the aggregation.

(b) Determination of collagen-induced blood-platelet aggregation

The A.D.P. solution is substituted with a collagen solution (bovine tendon extract).

(c) Results

Different groups of 20 rats each are used. Each group is orally administered a test derivative, at a dosage of 100 mg/kg. The results obtained during both tests are reported in following Table I which indicates the percent inhibition of blood-platelet aggregation obtained with respect to the reference group, 3 hrs after treatment.

TABLE I

| Treatment | Percent inhibition | |
|---|---|---|
| | A.D.P. | Collagen |
| derivative n°1 | 60.4 | 90.0 |
| derivative n°2 | 61.5 | 91.2 |
| derivative n°3 | 60.8 | 91.4 |
| derivative n°4 | 62.9 | 93.1 |
| derivative n°5 | 63.2 | 92.6 |
| derivative n°6 | 61.7 | 91.5 |
| derivative n°7 | 62.3 | 92.6 |
| derivative n°8 | 60.8 | 91.0 |
| derivative n°9 | 61.6 | 90.8 |
| derivative n°10 | 60.9 | 92.2 |
| derivative n°11 | 63.0 | 92.8 |
| derivative n°12 | 62.7 | 90.6 |
| derivative n°13 | 63.4 | 91.9 |
| derivative n°14 | 60.5 | 93.0 |
| derivative n°15 | 61.8 | 91.6 |

TABLE I-continued

| Treatment | Percent inhibition | |
|---|---|---|
| | A.D.P. | Collagen |
| derivative n°16 | 62.4 | 90.5 |
| derivative n°17 | 61.3 | 91.7 |
| derivative n°18 | 60.6 | 91.4 |

2. Anti-thrombotic properties

The technique used is based on that disclosed by FRIEDMAN (Amer. J. Med. Sci., 253, 83, 1967). After ether anesthesia and median laparotomy of female Wistar rats weighing 200-300 g, the vena cava inferior is exposed. A 1.8 cm long sharp metal helix is introduced in the lumen of the vessel at the level of the renal bifurcation and is "screwed" to the iliac veins. Five hours later, the animal is again anesthetized with ether. The vena cava inferior is ligated upstream and downstream of the helix, together with the collateral veins comprised between both ligations. The helix, together with the thrombus it retains, is removed after carefully opening the wall of the vena cava throughout the length involved; it is then dried by repeated dabbing with filter paper and is then weighed a first time. Immediately after, the thrombus is removed from the helix in a physiological saline bath, after which the helix is dried and is again weighed. The difference in weight gives the weight of the thrombus. On histological examination, said thrombi were found to be white thrombi.

The animals were treated by gastric intubation with the test derivatives of this invention, 48 hours, 24 hours and 2 hours prior to the implantation of the metal helix. The test samples were taken 5 hours after said implantation.

The results obtained are set forth in following Table II, in which are also reported the results of identical tests conducted with dipyridamole and acetyl salicylic acid which are usual reference materials, it being understood that the weight of the thrombus is the mean weight calculated from each series of 10 rats used for each test compound.

TABLE II

| Product administered | Dosage | Weight of the thrombus |
|---|---|---|
| Nil (Reference 1) | | 3.83 mg ± 0.16 |
| derivative n°1 | 100 mg/kg | 1.75 mg ± 0.22 |
| derivative n°2 | 100 mg/kg | 1.83 mg ± 0.27 |
| derivative n°3 | 100 mg/kg | 1.80 mg ± 0.32 |
| derivative n°4 | 100 mg/kg | 1.95 mg ± 0.17 |
| derivative n°5 | 100 mg/kg | 1.82 mg ± 0.20 |
| derivative n°6 | 100 mg/kg | 1.88 mg ± 0.24 |
| derivative n°7 | 100 mg/kg | 1.85 mg ± 0.16 |
| dipyridamole | 100 mg/kg | 3.75 mg ± 0.35 |
| acetylsalicyclic acid | 100 mg/kg | 2.98 mg ± 0.27 |
| Nil (Reference 2) | | 3.87 mg ± 0.25 |
| derivative n°8 | 100 mg/kg | 1.81 mg ± 0.31 |
| derivative n°9 | 100 mg/kg | 1.96 mg ± 0.21 |
| derivative n°10 | 100 mg/kg | 1.88 mg ± 0.28 |
| derivative n°11 | 100 mg/kg | 1.92 mg ± 0.24 |
| derivative n°12 | 100 mg/kg | 1.85 mg ± 0.18 |
| derivative n°13 | 100 mg/kg | 1.90 mg ± 0.20 |
| derivative n°14 | 100 mg/kg | 1.94 mg ± 0.29 |
| derivative n°15 | 100 mg/kg | 1.91 mg ± 0.30 |
| derivative n°16 | 100 mg/kg | 1.83 mg ± 0.25 |
| derivative n°17 | 100 mg/kg | 1.78 mg ± 0.24 |
| derivative n°18 | 100 mg/kg | 1.80 mg ± 0.17 |

The above results demonstrate the anti-thrombotic activity of the derivatives of this invention.

3. Anti-sludge properties

Said properties were investigated in vitro and in vivo in rats.

tube are then examined with a Mallasez cell, and the percent free red blood cells (RBC) and the percent agglomerates formed by 2, 3, 4, 5 ... RBC are noted. The results of this "preventive" treatment are given in following Table III, for the more active compounds.

TABLE III

| Size of agglomerates | | Controls | Derivative n°3 | | | | Derivative n°4 | | | | Derivative n°6 | | | |
|---|---|---|---|---|---|---|---|---|---|---|---|---|---|---|
| | | | 25 μg | 50 μg | 100 μg | 200 μg | 25 μg | 50 μg | 100 μg | 200 μg | 25 μg | 50 μg | 100 μg | 200 μg |
| 1 | Free RBC | 32 | 63 | 66 | 77 | 88 | 68 | 71 | 80 | 91 | 65 | 66 | 83 | 91 |
| 2 | Free RBC | 17 | 24 | 25 | 15 | 10 | 20 | 22 | 17 | 8 | 22 | 25 | 13 | 8 |
| 3 | Free RBC | 13 | 10 | 7 | 6 | 1 | 7 | 4 | 1 | 1 | 4 | 5 | 3 | 1 |
| 4 | Free RBC | 9 | 2 | 2 | 1 | 1 | 3 | 2 | 2 | | 5 | 3 | 0 | |
| 5 | Free RBC | 6 | 1 | | 1 | | 2 | 1 | | | 4 | 1 | 1 | |
| 6 | Free RBC | 3 | | | | | | | | | | | | |
| 7 | Free RBC | 4 | | | | | | | | | | | | |
| 8 | Free RBC | 4 | | | | | | | | | | | | |
| 9 | Free RBC | 3 | | | | | | | | | | | | |
| 10 | Free RBC | 3 | | | | | | | | | | | | |
| 11 | Free RBC | 2 | | | | | | | | | | | | |
| 12 | Free RBC | 3 | | | | | | | | | | | | |
| 13 | Free RBC | 1 | | | | | | | | | | | | |

| Size of agglomerates | | Controls | Derivative n°11 | | | | Derivative n°12 | | | | Derivative n°17 | | | |
|---|---|---|---|---|---|---|---|---|---|---|---|---|---|---|
| | | | 25 μg | 50 μg | 100 μg | 200 μg | 25 μg | 50 μg | 100 μg | 200 μg | 25 μg | 50 μg | 100 μg | 200 μg |
| 1 | Free RBC | 30 | 60 | 65 | 81 | 83 | 61 | 64 | 78 | 89 | 58 | 65 | 80 | 88 |
| 2 | Free RBC | 16 | 22 | 22 | 13 | 14 | 21 | 20 | 18 | 9 | 23 | 28 | 14 | 9 |
| 3 | Free RBC | 14 | 14 | 10 | 5 | 2 | 15 | 12 | 2 | 1 | 13 | 4 | 4 | 2 |
| 4 | Free RBC | 8 | 2 | 2 | 1 | 1 | 2 | 2 | 2 | 1 | 3 | 2 | 1 | 1 |
| 5 | Free RBC | 8 | 2 | 1 | | | 1 | 2 | | | 3 | 1 | 1 | |
| 6 | Free RBC | 4 | | | | | | | | | | | | |
| 7 | Free RBC | 3 | | | | | | | | | | | | |
| 8 | Free RBC | 4 | | | | | | | | | | | | |
| 9 | Free RBC | 4 | | | | | | | | | | | | |
| 10 | Free RBC | 3 | | | | | | | | | | | | |
| 11 | Free RBC | 3 | | | | | | | | | | | | |
| 12 | Free RBC | 2 | | | | | | | | | | | | |
| 13 | Free RBC | 1 | | | | | | | | | | | | |

RBC = Red blood cells

1. In vitro investigation

Red blood cells of rats are washed three times and diluted to 1/250 concentration in physiological saline. In each of 5 tubes are placed 0.6 ml of this suspension and 0.2 ml physiological saline. Into each tube is then added, respectively, an amount of 0, 25, 50, 100 and 200 μg of the test derivative contained in 0.2 ml of solution. After incubation for one hour at 37° C., 0.2 ml of a solution containing 125 μg/ml protamine sulfate is added thereto, and the resulting material is further incubated for 0.5 hour at 37° C. The red blood cells of each The test was repeated according to a "curative" procedure. The red blood cells were first contacted with the protamine sulfate and, after incubation for 0.5 hour, 0.2 ml containing 25 μg of the test derivative were added thereto, after which the material was further incubated for one hour at 37° C. The following results were obtained, the percent aggregates (as a function of size) being given in following TABLE IV.

TABLE IV

| Size of agglomerates | Reference tests | Derivative n°3 | Derivative n°4 | Derivative n°6 |
|---|---|---|---|---|
| 1 | 33 | 81 | 78 | 81 |
| 2 | 19 | 13 | 17 | 15 |
| 3 | 15 | 5 | 3 | 2 |
| 4 | 11 | 1 | 1 | 2 |
| 5 | 8 | | 1 | |
| 6 | 5 | | | |
| 7 | 3 | | | |
| 8 | 3 | | | |
| 9 | 3 | | | |
| 10 | | | | |

| Size of agglomerates | Reference tests | Derivative n°11 | Derivative n°12 | Derivative n°17 |
|---|---|---|---|---|
| 1 | 30 | 78 | 82 | 80 |
| 2 | 19 | 15 | 14 | 16 |
| 3 | 16 | 4 | 3 | 2 |
| 4 | 11 | 2 | 1 | 1 |
| 5 | 9 | 1 | | 1 |
| 6 | 6 | | | |
| 7 | 2 | | | |
| 8 | 4 | | | |
| 9 | 3 | | | |
| 10 | | | | |

2. In vivo investigation

Male Wistar rats weighing 200–300 g are anesthetized with pentobarbital (2.5 mg/kg, i.p.). After central laparotomy, an intestinal loop (with its mesenterium) is exteriorized and placed in a Ringer's solution at 37° C. contained in a Petri dish opened on an inverted microscope (25×10). Examination of the mesenteric arteries shows circulation to be normal. After administration of 25 mg/kg protamine sulfate by direct injection into the jugular vein, a sludge sets in, with stasis in several small arteries.

0.2 ml of a solution containing either 1 mg/ml or 0.1 mg/ml test derivative are then injected into the jugular vein. The controls are only administered physiological saline.

The results noted in 10 animals were as follows:

On injection of 1 mg/ml of compounds of this invention: disappearance within a period of time of 4–6 minutes of the punctiform sludge with concomitant reappearance of the parietal plasma flow and of the axial corpuscular flow;

On injection of 0.1 mg/ml: the same phenomenon is noted with respect to the punctiform sludge; normal flow, however, is somewhat less rapidly re-established.

Thus, it is apparent, from both in vitro and in vivo tests, that the derivatives of this invention possess a high anti-sludge activity.

4. Antalgic action.

(a) Mechanical stimulation method according to Haffner (Deutsch. Wish., 1959, 55, 731–733). This method comprises placing a pressure forceps at the base of the tail of a mouse and recording the number of bites self-inflicted by the animal in its endeavour to remove the forceps. The decrease of the number of bites prior and subsequent to oral administration of the test compound at a dosage of 100 mg/kg provides a measure of the antalgic activity of the derivatives of this invention. The mean percent antalgia thus determined as a function of time is given in following Table V.

TABLE V

| Derivatives | mean percent antalgia | | | |
|---|---|---|---|---|
| | after 30 min. | after 1 hr | after 2 hrs | after 3 hrs |
| 2 | 71 | 65 | 58 | 51 |
| 5 | 66 | 60 | 54 | 48 |
| 7 | 78 | 76 | 72 | 64 |
| 11 | 65 | 61 | 57 | 50 |
| 12 | 81 | 78 | 73 | 67 |
| 15 | 73 | 67 | 63 | 56 |
| 17 | 70 | 65 | 60 | 55 |

(b) Acetic acid method, according to Koster, Anderson & de Beer (Fed. Proced., 18, 1959, 412, 1, 626)

Intraperitoneal injection of a dilute acetic acid solution induces, in mice, characteristic writhing movements which are repeated due to the effect of pain.

Administration of derivatives of this invention to the animals of the treated group, at an oral dosage of 100 mg/kg, 30 minutes prior to intraperitoneal injection of acetic acid, shows that, with respect to the untreated reference group, the number of writhing movements is markedly decreased within the next thirty minutes.

The percent antalgia thus determined is 68 with derivative n°2, 64 with derivative n°5, 75 with derivative n°7, 71 with derivative n°11, 77 with derivative n°12, 69 with derivative n°15 and 68 with derivative n°17.

5. Anti-inflammatory action (a) Localized carrageenin-induced edema method 0.1 ml of a 1% carrageenin solution is injected at time O in the metatarsal flexor muscles of the right hind limb of rats.

The animals of the treated group are additionally orally administered 100 mg/kg of the test derivative, respectively one hour prior to, and then simultaneously with the phlogogenic agent, and then one hour and 2.5 hours thereafter. The determinations effected with a ROCH micrometer at times 0, 1 hr, 2 hrs, 3 hrs and 5 hrs after carrageenin administration make it possible to determine the percent anti-inflammatory activity, as a function of time. The results obtained are tabulated in following Table VI.

TABLE VI

| Derivatives | Percent anti-inflammatory activity | | |
|---|---|---|---|
| | after 1 hour | after 2 hours | After 3 hours |
| 2 | 36 | 47 | 53 |
| 5 | 39 | 51 | 55 |
| 7 | 44 | 55 | 63 |
| 11 | 41 | 50 | 58 |
| 12 | 42 | 54 | 61 |
| 15 | 40 | 52 | 57 |
| 17 | 37 | 49 | 54 |

(b) Ovalbumin-induced systemic edema method

Rats are administered a simultaneous intraperitoneal injection of 1 ml ovalbumin and 0.5 ml of a 1% aqueous Evans Blue solution. The animals of the treated group are additionally orally administered 100 mg/kg of the test derivative, one hour prior to ovalbumin administration and then simultaneously with said ovalbumin administration. The intensity of the phenomenon thus induced is rated according to a scale from 1 to 5, according to the progress of the inflammatory syndrome. The determinations are effected after 2 hours and after 3 hours. Thus are determined the mean intensity of the edema and the percent decrease of the edema reaction. The results obtained are set forth in following Table VII.

TABLE VII

| Derivatives | Percent decrease | |
|---|---|---|
| | After 2 hours | After 3 hours |
| 2 | 42 | 50 |
| 5 | 38 | 47 |
| 7 | 51 | 63 |
| 11 | 45 | 55 |
| 12 | 53 | 64 |
| 15 | 48 | 58 |
| 17 | 46 | 58 |

The good tolerance, the blood-platelet aggregation inhibiting activity, the anti-thrombotic, anti-sludge, antalgic and anti-inflammatory activity of the derivatives of this invention are apparent from the above toxicological and pharmacological investigations.

The therapeutic composition of this invention may be formulated for oral administration as tablets, coated tablets, capsules or drops. It may also be formulated for rectal administration as suppositories and, for parenteral administration, as injectable solutions.

Each unit dose contains advantageously 0.010 g to 0.250 g active ingredient in combination with therapeutically administrable excipients. The daily dosage regimen may vary from 0.010 g to 1.00 g active ingredient.

Non-limiting examples of pharmaceutical formulations of the composition of this invention are given below.

1. COATED TABLETS

Derivative n°1 ... 0.075 g
Excipient: corn starch, soluble starch, dicalcium phosphate, polyvinylpyrrolidone, magnesium stearate, talc, sugar, gum arabic, shellac, erythrosine, white wax, carnauba wax

2. SCORED TABLETS

Derivative n°4 ... 0.100 g
Excipient: starch, potato starch, sodium lauryl sulfate, magnesium stearate

3. CAPSULES

Derivative n°2 ... 0.150 g
Excipient: hydrated silica, talc, magnesium stearate

4. SUPPOSITORIES

Derivative n°5 ... 0.100 g
Semi-synthetic triglycerides, sufficient to make 1 suppository

5. INJECTABLE SOLUTION

Derivative n°7 ... 0.125 g

Isotonic solution, sufficient to make 5 ml

In view of their useful blood-platelet aggregation inhibiting properties, their anti-thrombotic, anti-sludge, antalgic and anti-inflammatory properties, the derivatives of this invention are usefully administrable therapeutically.

Because they prevent blood-platelet aggregation, they prevent the formation of white thrombus which is the starting point of arterial thrombosis.

They are applicable in the treatment of disorders of the cerebral and peripheral circulatory system, of coronary insufficiency and its complications, and for the prevention of the thrombosis-producing complications of atheroma.

In view of their antalgic and anti-inflammatory activity, the derivatives of this invention are useful in all inflammatory and pain processes, whatever the area involved and whatever the etiology of the inflammatory and pain phenomena to be treated. They are useful in rheumatology (for the treatment of inflammatory, degenerative or abarticular rheumatism), in otorhinolaryngology, in stomatology and in ophthalmology.

Having now described our invention what we claim as new and desire to secure by Letters Patent is:

1. Process for the preparation of a compound selected from the compounds having the formulae:

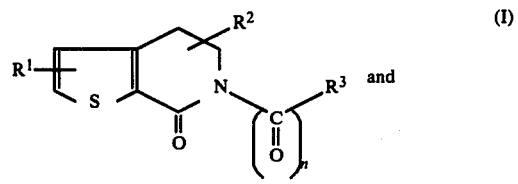

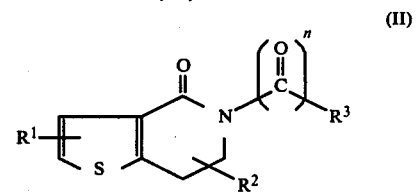

in which:

$R^1$ is selected from hydrogen, halogen, $C_{1-6}$ alkyl, $C_{1-6}$ alkoxy and $C_{1-6}$ alkylthio; $R^2$ is selected from hydrogen, $C_{1-6}$ alkyl, phenyl, carboxy, benzyloxycarbonyl and trimethoxybenzyloxycarbonyl; $R^3$ is selected from hydrogen, $C_{1-12}$ alkyl, phenyl, benzyl, benzyl substituted by one to three substituents selected from halogen, cyano, $C_{1-6}$ alkoxy and carbomethoxy; and n is selected from 0 and 1, and the therapeutically acceptable acid addition salts of said compounds, comprising oxidizing a compound selected from the compounds having the formulae (III) and (IV), respectively:

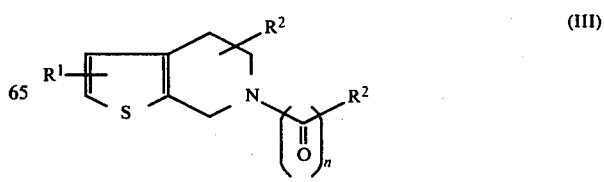

-continued

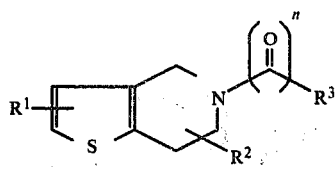

in which $R^1$, $R^2$, $R^3$ and n have the above-defined meanings, with an alkali metal permanganate, in acetone, at a temperature of 40°–56° C.

2. Therapeutic composition having bloodplatelet aggregation inhibiting properties, comprising an effective amount of a compound selected from the compounds having the formulae:

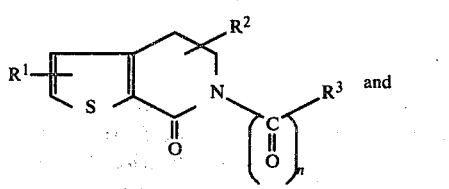

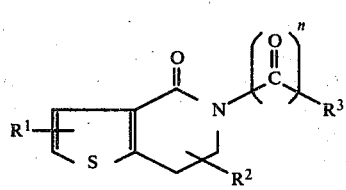

in which:
$R^1$ is selected from hydrogen, halogen, $C_{1-6}$ alkyl, $C_{1-6}$ alkoxy and $C_{1-6}$ alkylthio;
$R^2$ is selected from hydrogen, $C_{1-6}$ alkyl, phenyl, carboxy, benzyloxycarbonyl and trimethoxybenzyloxycarbonyl; $R^3$ is selected from hydrogen, $C_{1-12}$ alkyl, phenyl, benzyl, benzyl substituted by one to three substituents selected from halogen, cyano, $C_{1-6}$ alkoxy and carbomethoxy; and n is selected from 0 and 1; and their therapeutically acceptable acid addition salts, together with a pharmaceutically acceptable carrier.

3. Therapeutic composition as claimed in claim 2, in unit dosage form, each unit dose containing 0.010–0.250 g active ingredient.

4. Process for the preparation of a compound selected from the compounds having the formulae:

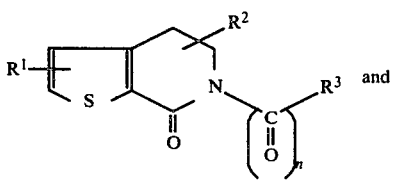

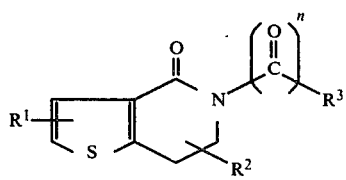

in which:
$R^1$ is selected from hydrogen, halogen, $C_{1-6}$ alkyl, $C_{1-6}$ alkoxy and $C_{1-6}$ alkylthio; $R^2$ is selected from hydrogen, $C_{1-6}$ alkyl, phenyl, carboxy, benzyloxycarbonyl and trimethoxybenzyloxycarbonyl; $R^3$ is selected from hydrogen, $C_{1-12}$ alkyl, phenyl, benzyl, benzyl substituted by one to three substituents selected from halogen, cyano, $C_{1-6}$ alkoxy and carbomethoxy; and n is selected from 0 and 1, and the therapeutically acceptable acid addition salts of said compounds, comprising oxidizing a compound selected from the compounds having the formulae (III) and (IV), respectively:

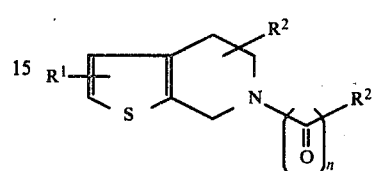

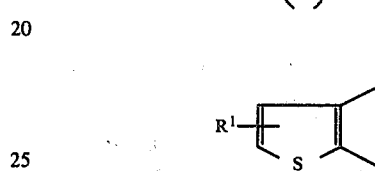

in which $R^1$, $R^2$, $R^3$ and n have the above-defined meanings, at room temperature within a two-phase water-benzene system, in the presence of a quaternary ammonium salt as phase transfer catalyst.

5. Therapeutic composition having anti-thrombotic and anti-sludge properties, comprising an effective amount of a compound selected from the compounds having the formulae:

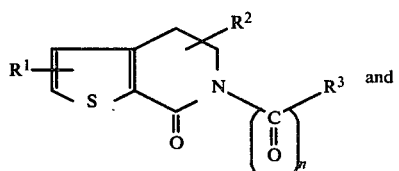

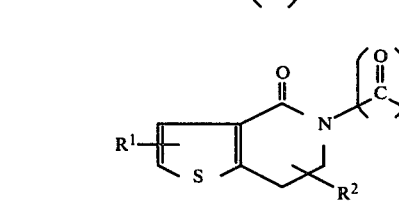

in which:
$R^1$ is selected from hydrogen, halogen, $C_{1-6}$ alkyl, $C_{1-6}$ alkoxy and $C_{1-6}$ alkylthio; $R^2$ is selected from hydrogen, $C_{1-6}$ alkyl, phenyl, carboxy, benzyloxycarbonyl and trimethoxybenzyloxycarbonyl; $R^3$ is selected from hydrogen, $C_{1-12}$ alkyl, phenyl, benzyl, benzyl substituted by one to three substituents selected from halogen, cyano, $C_{1-6}$ alkoxy and carbomethoxy; and n is selected from 0 and 1; and their therapeutically acceptable acid addition salts, together with a pharmaceutically acceptable carrier.

6. Therapeutic composition as claimed in claim 5, in unit dosage form, each unit dose containing 0.010–0.250 g active ingredient.

7. Therapeutic composition having antalgic properties, comprising an effective amount of a compound selected from the compounds having the formulae:

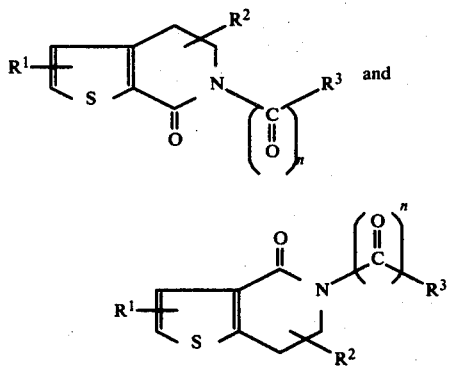

in which:
R$^1$ is selected from hydrogen, halogen, C$_{1-6}$ alkyl, C$_{1-6}$ alkoxy and C$_{1-6}$ alkylthio; R$^2$ is selected from hydrogen, C$_{1-6}$ alkyl, phenyl, carboxy, benzyloxycarbonyl and trimethoxybenzyloxycarbonyl; R$^3$ is selected from hydrogen, C$_{1-12}$ alkyl, phenyl, benzyl, benzyl substituted by one to three substituents selected from halogen, cyano, C$_{1-6}$ alkoxy and carbomethoxy; and n is selected from 0 to 1; and their therapeutically acceptable acid addition salts, together with a pharmaceutically acceptable carrier.

8. Therapeutic composition as claimed in claim 7, in unit dosage form, each unit dose containing 0.010–0.250 g active ingredient.

9. Therapeutic composition having anti-inflammatory properties, comprising an effective amount of a compound selected from the compounds having the formulae:

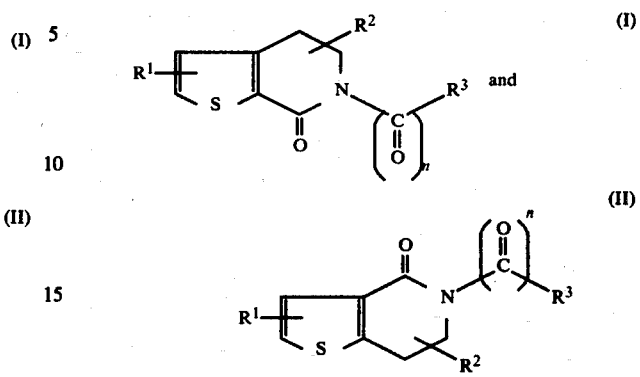

in which:
R$^1$ is selected from hydrogen, halogen, C$_{1-6}$ alkyl, C$_{1-6}$ alkoxy and C$_{1-6}$ alkylthio; R$^2$ is selected from hydrogen, C$_{1-6}$ alkyl, phenyl, carboxy, benzyloxycarbonyl and trimethoxybenzyloxycarbonyl; R$^3$ is selected from hydrogen, C$_{1-12}$ alkyl, phenyl, benzyl, benzyl substituted by one to three substituents selected from halogen, cyano, C$_{1-6}$ alkoxy and carbomethoxy; and n is selected from 0 and 1; and their therapeutically acceptable acid addition salts, together with a pharmaceutically acceptable carrier.

10. Therapeutic composition as claimed in claim 9, in unit dosage form, each unit dose containing 0.010–0.250 g active ingredient.

* * * * *